(12) United States Patent
King et al.

(10) Patent No.: US 7,875,191 B2
(45) Date of Patent: *Jan. 25, 2011

(54) BIOCIDE

(75) Inventors: Joseph A. King, Wayzata, MN (US); Marlin Frank, South Minneapolis, MN (US)

(73) Assignee: King Technology, Inc, Hopkins, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/315,285

(22) Filed: Dec. 2, 2008

(65) Prior Publication Data
US 2009/0092673 A1 Apr. 9, 2009

Related U.S. Application Data

(60) Continuation of application No. 11/999,654, filed on Dec. 6, 2007, now Pat. No. 7,501,067, which is a division of application No. 10/928,668, filed on Aug. 26, 2004, now Pat. No. 7,347,934.

(51) Int. Cl.
*C02F 1/50* (2006.01)
*C02F 1/76* (2006.01)
*C02F 103/42* (2006.01)

(52) U.S. Cl. .......................... 210/755; 210/764; 422/37; 424/618; 424/723

(58) Field of Classification Search .................. 210/755
See application file for complete search history.

(56) References Cited

U.S. PATENT DOCUMENTS

| | | | | |
|---|---|---|---|---|
| 5,882,526 A * | 3/1999 | Brown et al. | ................. | 210/753 |
| 6,120,698 A * | 9/2000 | Rounds et al. | ............... | 252/181 |
| 6,210,566 B1 * | 4/2001 | King | ..................... | 210/167.11 |
| 6,544,487 B1 * | 4/2003 | Ferguson et al. | ............. | 422/261 |
| 6,592,766 B2 * | 7/2003 | King | .......................... | 210/749 |
| 6,982,040 B2 * | 1/2006 | Costa et al. | .................. | 210/753 |
| 7,052,615 B2 * | 5/2006 | King et al. | ................... | 210/752 |
| 7,060,190 B2 * | 6/2006 | King et al. | ................... | 210/754 |
| 7,238,280 B1 * | 7/2007 | King | .......................... | 210/136 |
| 7,501,067 B2 * | 3/2009 | King et al. | .................. | 210/755 |

* cited by examiner

*Primary Examiner*—Peter A Hruskoci
(74) *Attorney, Agent, or Firm*—Jacobson & Johnson

(57) ABSTRACT

A two part biocide composition containing metal ions and bromine donor for killing microorganisms in a body of water and a method of killing microorganisms in a body of water by placing both metal ions and a bromine in the body of water to allow use of lower concentrations of bromine than if bromine were used alone as a biocide.

23 Claims, 1 Drawing Sheet

BIOCIDE

CROSS REFERENCE TO RELATED APPLICATIONS

This application is a continuation of application Ser. No. 11/999,654, filed Dec. 6, 2007, titled BIOCIDE (now U.S. Pat. No. 7,501,067), which is a division of application Ser. No. 10/928,668, filed Aug. 26, 2004, titled BIOCIDE (now U.S. Pat. No. 7,347,934).

FIELD OF THE INVENTION

This invention relates generally to water treatment and, more specifically, to the use of a biocide combination of a metal ion and bromine to kill harmful organisms in a body of water.

STATEMENT REGARDING FEDERALLY SPONSORED RESEARCH OR DEVELOPMENT

None

REFERENCE TO A MICROFICHE APPENDIX

None

BACKGROUND OF THE INVENTION

The concept of treating water with a chemical such as bromine to kill bacteria in a body of water is known in the art. Bromine offers the advantage of being slow dissolving to enable a time release of the bromine as well as being free of odors associated with other biocides. Typically, bromine is supplied in solid form. In addition, the use of metallic ions to kill bacteria in a body of water is also known in the art. In general the bromine concentration in the body of water should be maintained within a certain range to be effective. That is, if the concentration of bromine in a body of water is to low the ability to kill microorganisms is reduced or lost. On the other hand if the concentration of bromine in the water is to high it can be harmful to those who use the body of water. Typically, when bromine is added in solid form it is activated with an oxidizer to form hypobromous acid (HOBr) which kills the unwanted organisms.

A metallic ion such as a silver ion is an effective bactericide for a body of water including recreational water such as swimming pools, spas, jetted tubs or the like and is a preferred material because it is generally easier and safer to use than other bactericides or algaecides. A further advantage of using a silver ion is that it minimizes the need for pH adjustment of the body of water. However, if the concentration of metallic ions in a body of water is to low the ability to kill microorganisms is reduced or lost. On the other hand if the concentration of metallic ions is to high it can be harmful to those who use the body of water.

Oftentimes it is desired to use two or more biocides to kill microorganisms in a body of water in order to more effectively kill a wider variety of different microorganisms in the body of water. One of the difficulties is that when bromine is used in conjunction with a metal ion the metal ion and the bromine interact to reduce the effectiveness of the metal ion in killing microorganisms, oftentimes to a level that renders the metal ion concentration ineffective to kill microorganisms, thus negating the reason for using the two biocides.

When bromine is used separately in a body of water the bromine concentration can be controlled by the periodic release of bromine to the body of water from a bromine donor. Similarly, when a metallic ion is used, such as a silver ion, is used separately in a body water the silver ion concentration in the body of water can be maintained by the periodic release of a silver ions into the body of water from a silver ion donor. However, when two or more biocides or disinfectants such as a metal ion disinfectant is used in conjunction with bromine the level of metal ions in the water can be adversely affected so that the level of metal ions becomes insufficient to provide for effective control of microorganisms in the body of water thus rendering the combination impractical. Thus, the advantage of having metal ions in combination with bromine for use in treating a body is water is lost since the bromine can reduce the metal ion concentration in the water to levels that are ineffective to rid the body of water of microorganisms that normally would be killed by the presence of the metal ions.

The present invention is a discovery that with the use of a chelating agent the concentration of bromine and the concentration of a metal ion can both be maintained within effective microorganism killing regions when placed together in the same body of water and that the level of bromine can be maintained at lower concentration levels without diminishing the biocidal aspect of the combination.

SUMMARY OF THE INVENTION

Briefly, the present invention comprises a two part biocide composition containing a metal ion and bromine for killing microorganisms in a body of water and a method of killing microorganisms in a body of water by placing both metal ions and bromine in the body of water together with a chelating agent or placing both a metal ion donor and a bromine donor where the bromine is attached to a hydantoin group in the body of water to allow use of lower concentrations of bromine than if bromine were used alone as a biocide.

DESCRIPTION OF THE PREFERRED EMBODIMENT

Figure 1:
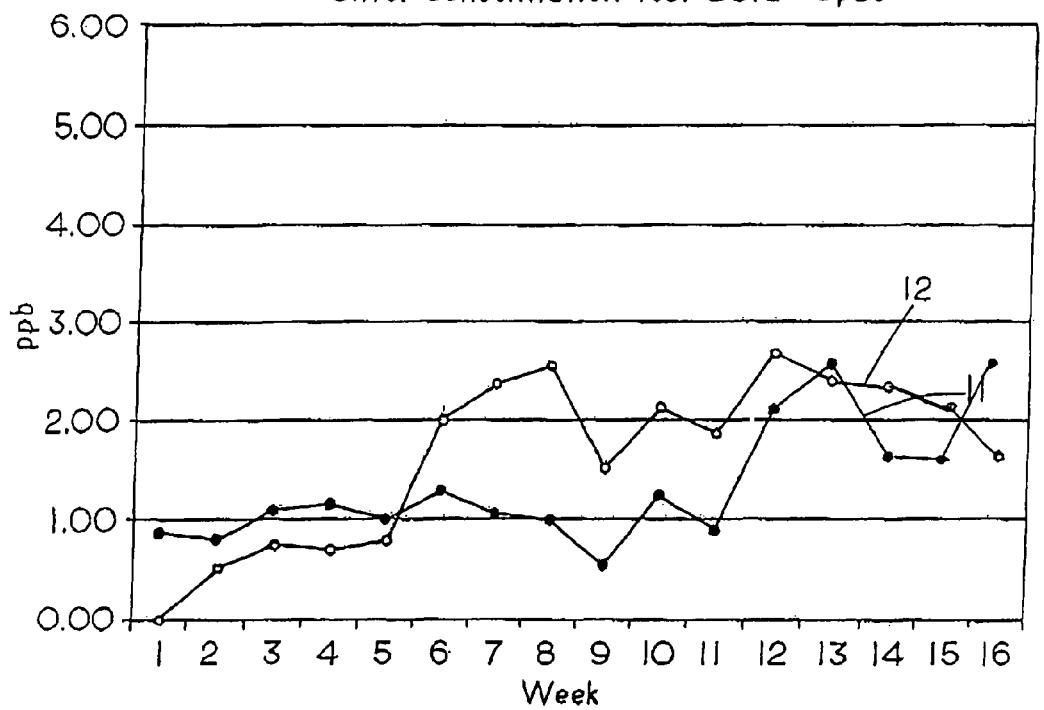
FIG. 1 is a graph of the levels of silver in a spa as a function of time.

When a halogen such as bromine is used as a disinfectant in a body of water such as in recreational water used in spas, pools, swimming pools, jetted bathtubs and other confined bodies of water one generally wants to maintain the concentration of the bromine in the range of 3-5 parts per million (ppm). Similarly, when a metal ion is used one generally wants to maintain the concentration of the metal ion in the range of 1-2 ppb. Calculations reveal that when metal ions and bromine are combined the bromine limits the available metal ions in the body of water to levels that are ineffective to control the microorganisms in the body of water.

The present invention has found that both the amount of bromine and amount of metal ions can be maintained in a body of water at effective levels to kill microorganism and that the combination can be maintained with levels of bromine that are less than if the bromine was used alone. That is, one may use 3-5 ppm of bromine when bromine is used alone but when bromine is used in conjunction with metal ions such as a silver ions one may need only 1-2 ppm of bromine.

In order to verify that the concentration of metal ions and concentration of bromine were maintained at effective levels three different bodies of water were supplied with bromine and a metal ion. The test results are as follows:

EXAMPLE

A cartridge containing a metal ion donor comprising limestone particles with some of the particles having a silver chloride coating was placed in a 300 gallon spa. The limestone particles were used for the carrier while the silver chloride became the silver ion donor. The cartridge contained approximately 57 grams of granular limestone coated with a polymer containing silver chloride. In addition to the silver ion donor bromine was added to the spa from a bromine donor. The bromine level was maintained at 1-2 ppm through the daily addition of a bromine donor comprising 1-bromo-3-chloro-5,5dimethylhydantion ($C_5H_6BrClN_2O_2$) which is available commercially in granular form under the tradename BromCide®. Approximately 14 grams of 1-bromo-3-chloro-5,5dimethylhydantion (BCDMH) was added daily to maintain the bromine concentration at levels of 1-2 ppm during bather use. The temperature of the spa was maintained at 102 degrees F. Two bathers used the spa for 30 minutes per day for 5 days per week. The level of silver ions in the spa was measured weekly. It was found that the level of silver ions in the spa ranged from about 1-3 ppb during the test. The pH was maintained in the range of 7.24 to 7.99 during the test.

Water samples were collected at weekly intervals for silver ion analysis. Water collection bottles contained nitric acid as a preservative and after sample collection the samples were maintained at approximately 4 degrees C. until delivered to a contract testing laboratory. Silver ion analyses was performed by Inductively Coupled Plasma Mass Spectrometry. The analysis were presumed to be specific for soluble silver due to the sample preparation steps. The level of bromine in the water was determined using the DPD Spectrophotometer Method. Water samples were collected in 125 ml flasks and 10 ml of the collected water was transferred to sample cells for analysis by HACH Method 8016 (Program 1300) using a HACH DR/4000 spectrophotometer. HACH DPD Total Chlorine Reagent was added to the 10 ml samples in the cells and reacted for three minutes. The results were automatically calculated and reported as mg/L (ppm).

FIG. 1 is a graph of the measured valves of silver ion in a 300 gallon spa and a 550 gallon spa. Reference numeral 11 identifies the silver ion concentration on a weekly basis in the 300 gallon spa and reference numeral 11 identifies the silver ion concentration on a weekly basis in the 550 gallon spa. In both cases the level of bromine was being maintained at a level of 1-2 ppm. As can be seen from the graph, after initial start up the concentration of silver ions ranged from about 1 ppb to 3 ppb. The combination proved effective in killing microorganism and lacked the odor associated with a halogen such as chlorine.

In the present invention the use of the chelating agent 1-bromo-3-chloro-5,5 dimethylhydantion (BCDMH), which is commercially available under in either gel, solid, granules or tablets form performed a dual purpose since the chelating agent contained the bromine for release into the water as well as preventing the reduction of the level of silver ions. Other chelating agents such as 1,3 dichloro-5,5 dimethylhydantion and 1,3 dibromo-5,5 dimethylhydantion are also suitable for use in the present invention. The use of the chelating agent and particularly a chelating agent with bromine attached to a hydantoin group was found to provide a two part disinfectant or biocide where the levels of bromine could be maintained at effective antimicroorganism levels which were equal or less than the effective antimicroorganism levels of the bromine when used alone. By antimicroorganism levels it is understood to mean that the levels of the biocide are sufficient to kill the microorganisms in the body of water.

While 1-bromo-3-chloro-5,5dimethylhydantion (BCDMH) is a preferred chelating agent and bromine donor since it carries the bromine attached to a hydantoin group. However, other chelating agents where the bromine is not part of the chelating agent can also be used in conjunction with a separate bromine donor and metal ion donor For example, the use of a bromine donor comprising bromine in stick or other form can be used to release the bromine into the body of water if a separate chelating agent such as anthranilate, saccharinate or sulfadiazine is present in the body of water with the metal ions or a metal ion donor.

Figure 2:
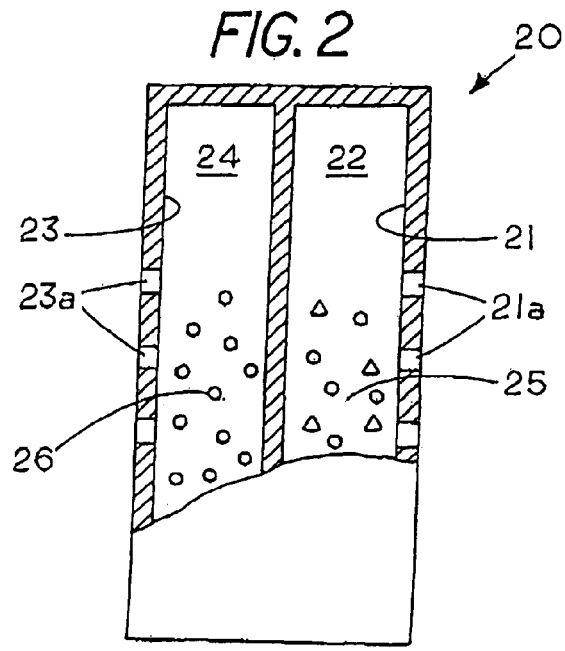
FIG. 2 is a cutaway view of a dispenser containing a bromine donor and a metal ion donor.

FIG. 2 shows a dispenser 20 having a first housing 21 containing a compartment 22 and a second housing 23 with a compartment 24 therein. Located in compartment 22 is a bromine donor 25 and located in compartment 24 is a silver ion donor 26. A set of openings 21a allows water access to compartment 22 and to the bromine donor 25. Similarly, a set of openings 23a allows water access to compartment 24 and the silver ion donor 26. The present invention included step of placing a dispenser 20 container both a bromine donor 25 and a silver ion donor 26 in the body of water and allowing water to come into contact with the bromine donor 25 and the silver ion donor 26 to periodically release bromine and silver ions into the body of water. A measurement of the microbial activity in the body of water demonstrated that with even though the bromine concentrations was less than normally used the combination of the lower bromine and the silver ion produced an effective disinfectant for a body of contained water making it a suitable disinfectant for common recreational bodies of water such as spas and pools. Thus one feature of the invention is the use of a chelating agent selected from the group consisting of 1-bromo-3-chloro-5,5dimethylhydantion, 1,3 dichloro-5,5 dimethylhydantion, 1,3 dibromo-5,5 dimethylhydantion, anthranilate, saccharinate and sulfadiazine.

While numerous factors influences the concentration of disinfectants in bodies of water such as pools, spas and the like the EPA provides Efficacy Data Requirements for bodies of water such as Swimming Pool Water Disinfectants which are spelled out in EPA DIS/TSS-12/Apr. 23, 1979, and are herein incorporated by reference. The present invention provides a cooperative two component biocide in a body of water that generates bromine and silver ions in concentrations that are effective in maintaining the microorganisms at levels below the unacceptable levels specified in EPA DIS/TSS-12/Apr. 23, 1979. More specifically, in one embodiment of invention a cooperative biocide composition releases bromine with a concentration of released bromine in a body of water ranging from about 1 ppm to 2.3 ppm in the body of water in the presence of a silver ion in the body of water with a silver ion concentration ranging from about 1 ppb of silver ions to about 3 ppb of silver ions with the cooperative biocide combination effective to control microorganisms to thereby permit safe recreational use of the body of water with the released concentrations maintaining the level of harmful microorganisms below unacceptable levels specified in EPA DIS/TSS-12/Apr. 23, 1979.

In addition, the invention includes the method of disinfecting a body of water with at least two biocides with at least one of the biocides maintainable at a lower concentration level when used in combination then if used alone with the released concentrations maintaining the level of microorganisms below the unacceptable levels specified in EPA DIS/TSS-12/Apr. 23, 1979. More specifically, the method includes releasing bromine into the body of water in sufficient amounts to maintain the bromine concentration in a range of about 1 ppm to about 2.3 ppm when in the presence of a concentration of silver ions in a range of about 1 ppb to about 3 ppb with the silver ions and the bromine effective to provided a disinfected body of water for recreational use with the level of harmful microorganisms below unacceptable levels specified in EPA DIS/TSS-12/Apr. 23, 1979.

Thus in the present invention a spa, pool or other contained fluid for recreational use contains a body of water; a level of bromine present in the amount of 1 to 2.3 ppm; and a level of silver ions present in the amount of 1 to 3 ppb with the bromine and the silver ions cooperating to maintain a standard plate count of less than 200 colonies per milliliter and more specifically the bromine and the silver ions cooperating to maintain a standard plate count at 35 degrees F. of less than 200 colonies per milliliter.

Thus one method of treating a body of water is to add a N-halohydantoin derivative such as 1,3 dichloro-5,5 dimethylhydantion, 1,3 dibromo-5,5 dimethylhydantion or 1-bromo-3-chloro-5,5 dimethylhydantion to a body of water that includes a silver ion released from a silver ion donor such as silver chloride.

We claim:

1. A method of treating a body of water to kill microorganisms by maintaining an effective concentration of at least two different biocides comprising:
    adding metal ions comprising adding a silver ion donor to the body of water to maintain a metal ion concentration effective to kill microorganisms;
    adding sufficient bromine to the body of water to maintain a bromine concentration effective to kill microorganisms; and
    adding an agent that maintains the effectiveness of the metal ions in killing microorganisms and the effectiveness of the bromine in killing microorganisms, said agent consisting of 1-bromo-3-chloro-5,5dimethylhydantion, 1,3 dichloro-5,5 dimethylhydantion, or 1,3 dibromo-5,5 dimethylhydantion.

2. The method of claim 1 wherein the bromine content is maintained at 1-2 ppm by the addition of a bromine donor comprising 1-bromo-3-chloro-5, 5 dimethylhydantion.

3. The method of claim 1 wherein the metal ion concentration is maintained at 1-2 ppb of silver ions by adding the silver ion donor to the body of water.

4. The method of claim 1 wherein the metal ion concentration is maintained at 1-3 ppb of silver ions.

5. The method of claim 1 where the step of adding sufficient bromine to the body of water and adding the agent comprises adding 1-bromo-3-chloro-5,5dimethylhydantion, or 1,3 dibromo-5,5 dimethylhydantion to the body of water.

6. The method of claim 1 wherein the step of adding a silver ion donor to the body of water comprises adding silver chloride.

7. The method of claim 6 wherein the silver chloride is coated on particles of limestone before placing in the body of water.

8. The method of claim 1 wherein the method of treating a body of water comprises treating a body of recreational water for at least partial human immersion therein.

9. The method of claim 1 including the step of placing a dispenser containing both a bromine attached to said agent and the silver ion donor in the body of water and allowing water to come into contact with both the bromine attached to said agent and the silver ion donor.

10. A method of treating a body of water by maintaining an effective concentration of at least two biocides comprising:
    placing a metal ion donor comprising a silver ion donor in a body of water to maintain a silver ion concentration effective to kill microorganisms in the body of water;
    placing an agent that maintains the effectiveness of the at least two different biocides in killing microorganisms in the body of water, said agent consisting of 1-bromo-3-chloro-5,5dimethylhydantion, 1,3 dichloro-5,5 dimethylhydantion, 1,3 dibromo-5,5 dimethylhydantion, anthranilate, saccharinate or sulfadiazine; and
    placing bromine in the body of water in sufficient amounts to maintain a bromine concentration effective to kill microorganisms, wherein the agent maintains the effectiveness of the metal ions in killing microorganisms and the effectiveness of the bromine in killing microorganisms.

11. The method of claim 10 wherein the step of placing a metal ion donor and the bromine in the body of water comprises placing the metal ion donor and the bromine in a dispenser before placing the bromine and the metal ion donor in the body of water.

12. The method of claim 10 wherein the step of placing the silver ion donor in the body of water comprises placing the silver ion donor in a dispenser that is placed in the body of water and the bromine is attached to the agent.

13. The method of claim 12 wherein the step of placing the bromine in the body of water comprises first placing the bromine in a dispenser.

14. The method of claim 12 wherein the step of placing a metal ion donor comprises placing silver chloride on a carrier in the dispenser.

15. A method of treating a body of water with at least two biocides comprising;
    placing a bromine donor comprising an agent that maintains the effectiveness of the at least two different biocides in killing microorganisms in a body of water, wherein the biocides are the bromine donor and a metal ion donor; and
    placing a metal ion donor in the body of water and allowing the bromine and the metal ions to simultaneously disperse into the body of water to kill microorganisms in the body of water wherein the metal ion donor releases silver ions and the bromine donor is 1-bromo-3-chloro-5,5dimethylhydantion, 1 or 1,3 dibromo-5,5 dimethylhydantion.

16. The method of claim 15 wherein the step of placing a bromine donor comprises placing 1-bromo-3-chloro-5,5 dimethylhydantion in the body of water.

17. The method of claim 15 wherein the step of placing a metal ion donor comprises placing silver chloride in the body of water.

18. The method of claim 15 wherein the method of treating a body of water comprises treating a body of recreational water.

19. The method of claim 18 wherein the method of treating a body of recreational water comprises treating water in a spa, hot tub or swimming pool by maintaining the level of silver ions at 1-3 ppb and the level of bromine at 1-2ppm.

20. The method of claim 15 wherein the method of treating a body of water comprises treating water in a jetted bath tub.

21. The method of claim 15 wherein the body of water is maintained at about 102 degrees F.

22. A method of disinfecting a body of water with at least two biocides with at least one of the biocides maintainable at a lower concentration level when used in combination then if used alone comprising:
    adding a silver ion donor into the body of water;
    adding into the body of water a N-halohydantoin derivative that maintains the effectiveness of at least two different biocides in killing microorganisms, wherein the biocides are the silver ion donor and bromine; and
    releasing bromine into the body of water in sufficient amounts to maintain the bromine concentration in a range of about 1 ppm to about 2.3 ppm when in the presence of a concentration of silver ions in a range of about 1 ppb to about 3 ppb with the silver ions and the bromine effective to provided a disinfected body of water for recreational use.

23. The method of claim 22 wherein the N-halohydantoin derivative consists of 1,3 dibromo-5,5 dimethylhydantion or 1-bromo-3-chloro-5,5 dimethylhydantion.

* * * * *